(12) United States Patent
 Bromer

(10) Patent No.: US 9,597,091 B2
(45) Date of Patent: Mar. 21, 2017

(54) ARTICULATED BONE DRILL AND TAP

(71) Applicant: EMPIRE TECHNOLOGY DEVELOPMENT LLC, Wilmington, DE (US)

(72) Inventor: Nicholas S. Bromer, Marietta, PA (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 405 days.

(21) Appl. No.: 14/118,626

(22) PCT Filed: May 13, 2013

(86) PCT No.: PCT/US2013/040720
§ 371 (c)(1),
(2) Date: Nov. 19, 2013

(87) PCT Pub. No.: WO2014/185887
PCT Pub. Date: Nov. 20, 2014

(65) Prior Publication Data
US 2014/0336653 A1    Nov. 13, 2014

(51) Int. Cl.
 *A61B 17/16* (2006.01)
(52) U.S. Cl.
 CPC ...... *A61B 17/1617* (2013.01); *A61B 17/1637* (2013.01); *A61B 17/1642* (2013.01); *A61B 17/1655* (2013.01); *A61B 17/1631* (2013.01)
(58) Field of Classification Search
 CPC ............ A61B 17/1631; A61B 17/1637; A61B 17/1642; A61B 17/1655
 See application file for complete search history.

(56) References Cited

U.S. PATENT DOCUMENTS 4,706,659 A * 11/1987 Matthews ............ A61B 17/164
                                                            464/173
4,713,077 A    12/1987 Small
5,190,551 A    3/1993 Chin
5,842,865 A    12/1998 Bassett
(Continued)

FOREIGN PATENT DOCUMENTS

EP    1044314    3/2005
WO    0160232    8/2001
(Continued)

OTHER PUBLICATIONS

International Searching Authority, International Search Report and Written Opinion for PCT/US13/40720, Aug. 9, 2013, 14 pages.

*Primary Examiner* — Nicholas Woodall
(74) *Attorney, Agent, or Firm* — Jensen & Puntigam, P.S.

(57) ABSTRACT

Technologies related to articulated bone drill and articulated bone tap apparatus are generally described. In some examples, articulated bone drills and taps may comprise bendable spines, movable bits, and flexible cylindrical tap or drill sleeves. The movable bit may be engaged at a distal end of the spine, and tensioning the spine and/or longitudinal displacement of at least one spine section with respect to at least one other spine section may be effective to steer the bit. The flexible cylindrical sleeve may be adapted to at least partially encase the spine, and the sleeve and the bit may be mechanically engaged so that rotation of the sleeve around the spine is effective to rotate the bit.

28 Claims, 7 Drawing Sheets

(56) References Cited

U.S. PATENT DOCUMENTS

| | | |
|---|---|---|
| 5,908,423 A | 6/1999 | Kashuba |
| 7,722,678 B2 | 5/2010 | Brown |
| 7,766,264 B2 | 8/2010 | Lesar |
| 8,133,225 B2 | 3/2012 | Pieske |
| 8,151,908 B2 | 4/2012 | Swinford |
| 8,231,629 B2 | 7/2012 | Lerner |
| 8,282,638 B2 | 10/2012 | Choe |
| 2002/0029055 A1* | 3/2002 | Bonutti ............... A61B 10/025 606/170 |
| 2003/0018333 A1* | 1/2003 | Kokesh ............... A61B 17/685 606/53 |
| 2004/0138663 A1 | 7/2004 | Kosashvili |
| 2004/0249389 A1 | 12/2004 | Kim |
| 2010/0292695 A1* | 11/2010 | May ................... A61B 17/1642 606/64 |
| 2011/0218538 A1 | 9/2011 | Sherman |
| 2012/0191094 A1 | 7/2012 | Alain |
| 2012/0191095 A1* | 7/2012 | Burger ............... A61B 17/1642 606/80 |
| 2013/0012942 A1 | 1/2013 | Nelson |

FOREIGN PATENT DOCUMENTS

| | | |
|---|---|---|
| WO | 02087813 | 11/2002 |
| WO | 03002841 | 1/2003 |
| WO | 03009744 | 2/2003 |
| WO | 03034953 | 5/2003 |
| WO | 2008144709 | 11/2008 |
| WO | 2009151801 | 12/2009 |
| WO | 2012151396 | 11/2012 |
| WO | 2013052807 | 4/2013 |

\* cited by examiner

ARTICULATED BONE DRILL AND TAP

CROSS-REFERENCE TO RELATED APPLICATIONS APPLICATION

This application is a U.S. national stage filing under 35 U.S.C. 371 of international application PCT/US13/40720, entitled "ARTICULATED BONE DRILL AND TAP", filed on 13 May 2013, which is incorporated by reference herein in its entirety.

BACKGROUND

Unless otherwise indicated herein, the materials described in this section are not prior art to the claims in this application and are not admitted to be prior art by inclusion in this section.

Orthopedics, the branch of medicine that deals with the prevention and correction of injuries or disorders of the skeletal system and associated muscles, joints, and ligaments, has seen a variety of advances over the years. However, inadequate reduction and fixation of bones remains a problem in the treatment of bone injuries. This is particularly true for bones of complex shape, such as the human pelvis and jaw (mandible) bones, although depending on the nature of and circumstances of injury, difficulties can arise in treating any bones.

SUMMARY

The present disclosure generally describes technologies including apparatus and methods relating to articulated bone taps and/or articulated bone drills. Some example articulated bone tap apparatus may comprise a bendable spine, a movable bit, and a flexible cylindrical tap sleeve. The bendable spine may have a proximal end, a distal end, and a longitudinal axis, and may comprise two or more sections extending from the proximal end along the longitudinal axis to the distal end. The movable bit may be engaged at the distal end of the spine, and tensioning the spine and/or longitudinal displacement of at least one spine section with respect to at least one other spine section may be effective to steer the bit. The flexible cylindrical tap sleeve may be adapted to at least partially encase the spine, and the tap sleeve and the bit may be mechanically engaged so that rotation of the tap sleeve around the longitudinal axis of the spine is effective to rotate the bit. For example, the tap sleeve may be adapted to encase the spine between the bit and a proximal sleeve section at the proximal end of the spine, and the tap sleeve may comprise rigid cylindrical tap sections arranged end to end along the spine, each tap section comprising an internal bore configured to house the spine, and each tap section comprising an external tap flute configured to cut a spiral groove into a sidewall of a hole cut by the bit as the sleeve rotates.

Some example articulated bone drill apparatus may comprise a bendable spine, a movable bit, and a flexible cylindrical drill sleeve, where the drill sleeve may replace the tap sleeve of the articulated bone tap apparatus introduced herein. The drill sleeve may comprise rigid cylindrical drill sleeve sections arranged end to end along the spine, where the drill sleeve sections may for example omit the external tap flutes of the tap sections as described herein.

Some example methods for treating bone fractures or dislocations may comprise drilling a hole in a first compact bone wall of a first bone; inserting an articulated bone tap apparatus in the hole in the first compact bone wall; turning the articulated bone tap apparatus to advance the articulated bone tap apparatus through a non-linear path within cancellous bone in the first bone to a second compact bone wall of the first bone; turning the articulated bone tap apparatus to advance the articulated bone tap apparatus through the second compact bone wall of the first bone and to tap a hole in the second compact bone wall of the first bone by cutting a spiral thread groove in a sidewall of the hole in the second compact bone wall of the first bone; and anchoring hardware in the tapped hole in the second compact bone wall of the first bone, wherein the hardware is adapted to apply one or more of a compressive force to a fracture in the first bone, or a compressive force between the first bone and a dislocated second bone.

Example methods may include the use of articulated bone drill apparatus disclosed herein. For example, methods may include inserting an articulated bone drill apparatus in the hole in the first compact bone wall; turning the articulated bone drill apparatus to advance the articulated bone drill apparatus through the non-linear path within cancellous bone in the first bone to the second compact bone wall of the first bone; turning the articulated bone drill apparatus to drill the hole in the second compact bone wall of the first bone; and/or removing the articulated bone drill apparatus from the first bone.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1:
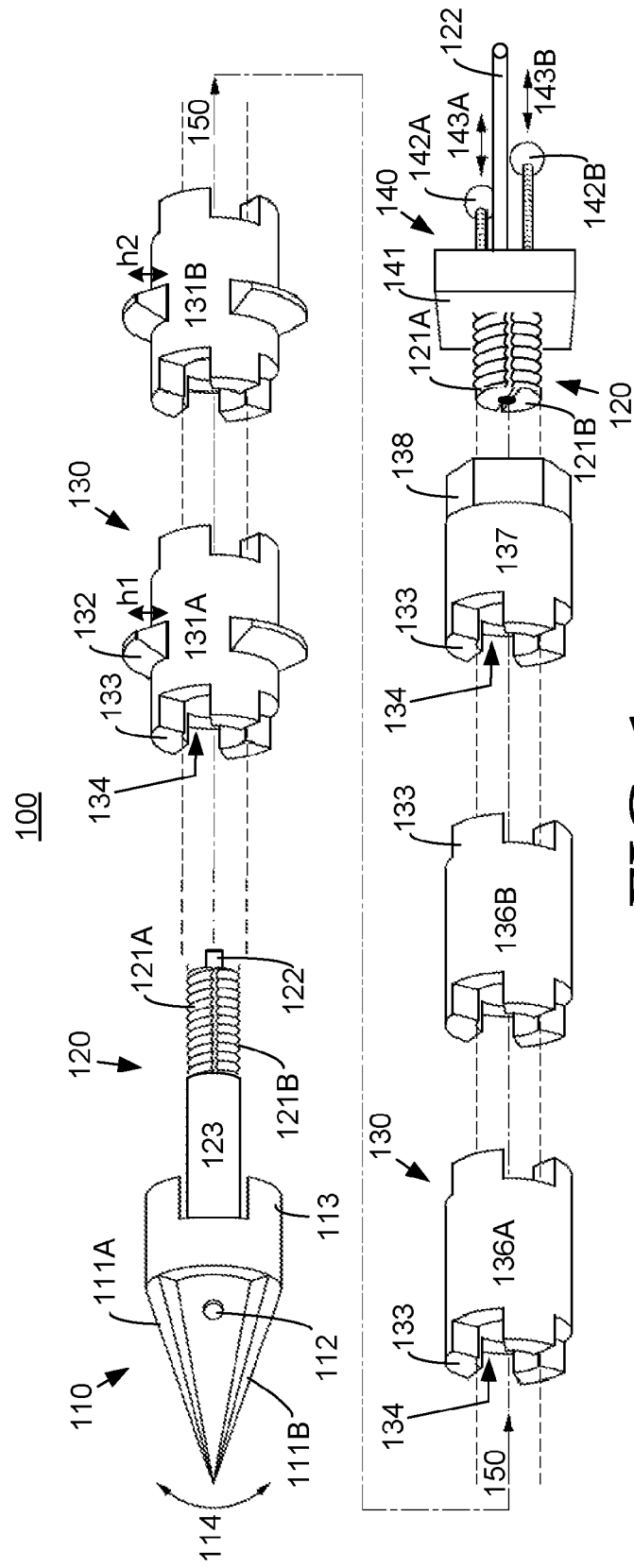
FIG. 1 is a diagram illustrating an exploded view of an example articulated bone tap apparatus.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, may be arranged, substituted, combined, and designed in a wide variety of different configurations, all of which are explicitly contemplated and made part of this disclosure.

The present disclosure is generally drawn, inter alia, to technologies including methods, devices, and/or systems relating to articulated bone drills and articulated bone taps. In some examples, articulated bone drills and taps may comprise bendable spines, movable bits, and flexible cylindrical tap or drill sleeves. The movable bit may be engaged at a distal end of the spine, and tensioning the spine and/or longitudinal displacement of at least one spine section with respect to at least one other spine section may be effective to steer the bit. The flexible cylindrical sleeve may be adapted to at least partially encase the spine, and the sleeve and the bit may be mechanically engaged so that rotation of the sleeve around the spine is effective to rotate the bit.

FIG. 1 is a diagram illustrating an exploded view of an example articulated bone tap apparatus, arranged in accordance with at least some embodiments of the present disclosure. Example articulated bone tap apparatus 100 comprises a movable bit 110, a bendable spine 120, a flexible cylindrical tap sleeve 130, and a steering nut 140. Generally speaking, a tap is a tool for cutting threads. Embodiments of this disclosure may include a specially adapted tap apparatus 100, which is adapted for bone repair, and especially for repair of curved bones such as the human pelvis and mandible. Articulated bone tap apparatus 100 may comprise a plurality of articulated sleeve sections 131A, 131B, 136A, 136B and 137 allowing apparatus 100 to assume a curved shape. Apparatus 100 may include movable bit 110 so that apparatus 100 can progress through bone. Apparatus 100 may also have controlled flexibility so that it can follow a path through a curved flat bone such as the ilium or the pubic bone. All bones are characterized by outer hard "compact" bone and softer interior "cancellous" bone (marrow). Embodiments of apparatus 100 may use this bony structure, in part, to guide apparatus 100 through cancellous bone from an entry point to a fracture or a bone dislocation. There, the apparatus 100 may be embedded into compact bone to stabilize the injury, optionally after closed reduction.

In FIG. 1, bit 110 is engaged at a distal end of the spine 120, and spine 120 has a proximal end at steering nut 140 and a longitudinal axis 150 extending between the proximal and distal ends. A middle portion of spine 120 is not illustrated in FIG. 1 to allow better visibility of sleeve 130. Spine 120 comprises a head section 123 by which spine 120 is coupled to bit 110, and sections 121A and 121B extending along the longitudinal axis 150 between the head section 123 at the distal end and the steering nut 140 at the proximal end. Longitudinal displacement of a spine section, e.g., spine section 121A, with respect to at least one other spine section, e.g., spine section 121B, may be effective to steer the bit 110 by changing an angle 114 of the bit 110. In some embodiments, spine sections 121A and 121B may "merge" or be joined into a single, undivided head section 123 at a short distance away from the bit 110 as shown, to allow for a single coupling between spine 120 and bit 110, while still providing for steering bit 110 by adjusting spine sections 121A and 121B. It will be appreciated that while two spine sections 121A and 121B are illustrated in FIG. 1, additional spine sections may be used in some embodiments.

Figure 7:
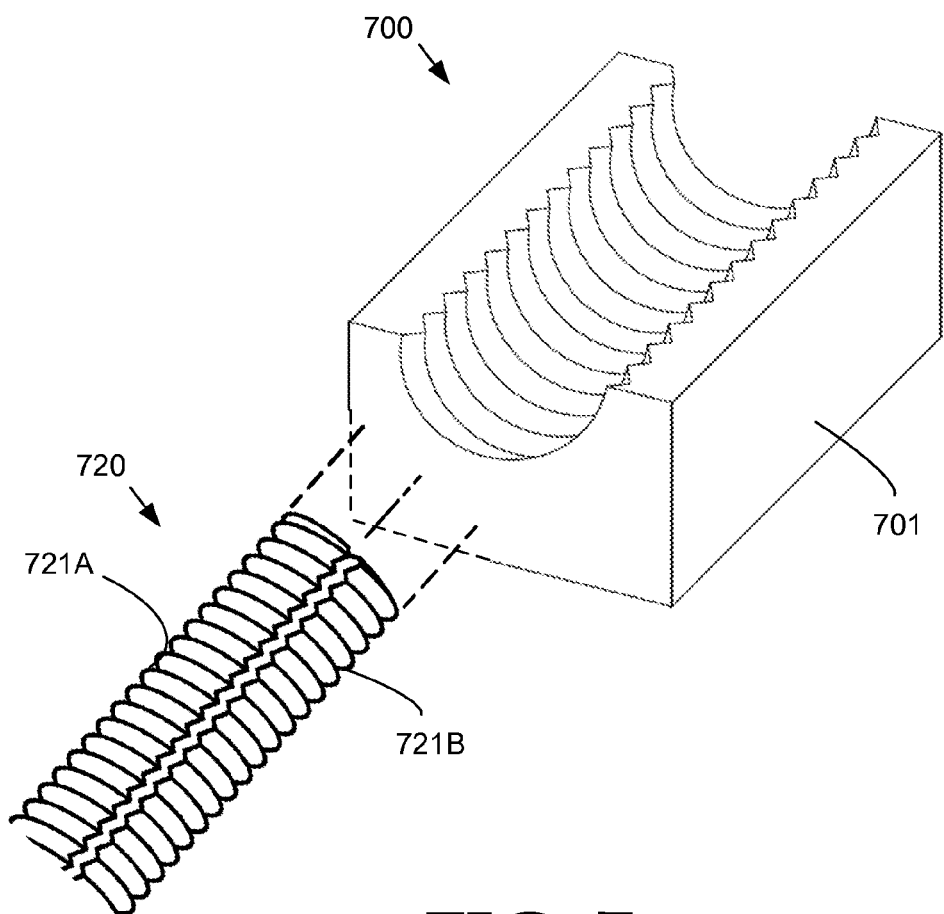
FIG. 7 is a diagram illustrating a perspective view of an example split nut adapted for use as a steering nut.

Steering nut 140 may be effective to longitudinally displace spine section 121A with respect to other spine section 121B, and vice versa, to steer the bit 110. For example, in one arrangement, shown in FIG. 1, steering nut 140 may comprise a base 141 and pulls 142A and 142B. Spine section 121A may be displaced with respect to other spine section 121B by adjusting pull 142A as illustrated by adjustment 143A. Similarly, spine section 121B may be displaced with respect to spine section 121A by adjusting pull 142B as illustrated by adjustment 143B. In some embodiments, both pulls 142A and 142B may be operated together to steer the bit 110. In some embodiments, steering nuts may be configured in a "split nut" arrangement such as illustrated in FIG. 7.

Spines such as spine 120 comprising multiple sections 121A and 121B are an optional feature which need not be included in all embodiments. In some embodiments, a spine may comprise a single longitudinal section (not illustrated) that may be tensioned and relaxed to increase or decrease the stiffness (bendability) of apparatus 100. The bendability of apparatus 100 can vary with the tensioning/relaxation of a spine because the axial force between adjacent sections of the sleeve 130 can affect the overall stiffness of the apparatus 100, as the joints between the sections of the sleeve 130 tend to align axially when forced together.

Figure 3:
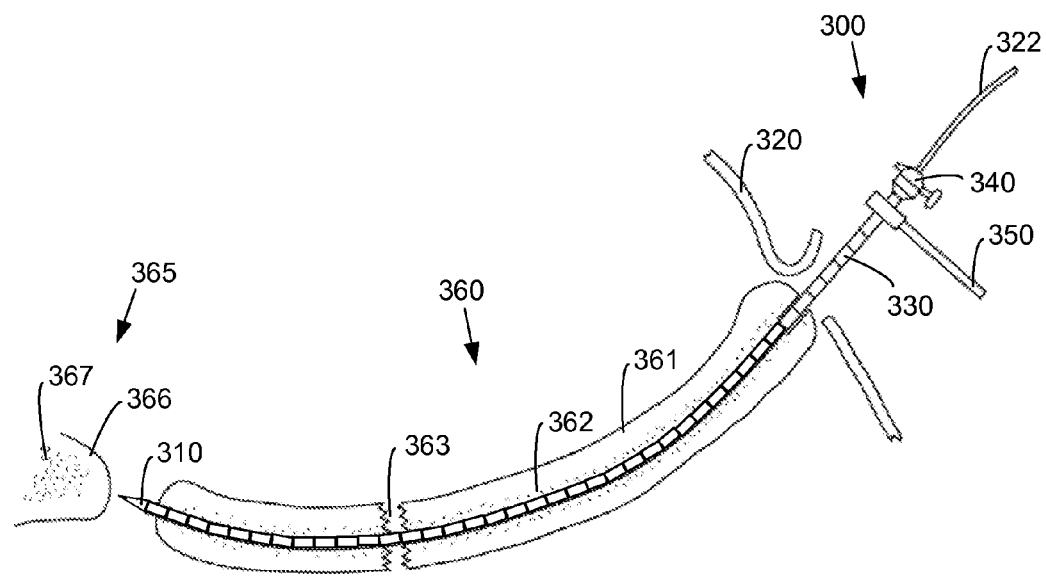
FIG. 3 is a diagram illustrating an example articulated bone tap or drill apparatus disposed in a bone.

Furthermore, in some embodiments, a spine may not be involved in steering the apparatus 100; instead, apparatus 100 may be effectively guided by compact bone walls to either side of apparatus 100, e.g., as illustrated in FIG. 3. An apparatus 100 which is inserted into a bone at a certain point and is oriented in a certain direction, e.g., as apparatus 300 is inserted into the right side of bone 360 in FIG. 3, will tend to progress toward a certain point, e.g., toward the left end of bone 360 as illustrated in FIG. 3. However, the initial aim of apparatus 100 may not be completely accurate and/or the trajectory of apparatus 100 might be thrown off by random effects or person-to-person variation. Therefore, some embodiments may optionally include a steering mechanism. The spine 120, as mentioned above, can be split down the middle into sections 121A and 121B. Also, the spine 120 may optionally be tensioned to exert a compressive force on the sleeve sections 131A, 131B, 136A, 136B, and 137, to change the stiffness of the apparatus 100. In some embodiments, tension-based steering can be combined with a steering nut 140, which may be configured as illustrated in FIG. 1, or may comprise for example a split nut as described in connection with FIG. 7.

Tap sleeve 130 may be adapted to at least partially encase spine 120. For example, spine 120 may extend through a central bore 134 of tap sleeve 130. Tap sleeve 130 and bit 110 may be mechanically engaged so that rotation of tap sleeve 130 around longitudinal axis 150 of spine 120 is effective to rotate bit 110. For example, in some embodiments, cogs 133 on tap section 131A may engage cogs 113 on bit 110 to mechanically engage tap sleeve 130 and bit 110.

In some embodiments, as illustrated in FIG. 1, tap sleeve 130 may be adapted to encase the spine 120 between the bit 110 and a proximal sleeve section 137 at the proximal end of the spine 120. Tap sleeve 130 may comprise a plurality of rigid cylindrical sleeve sections, e.g., tap sections 131A, 131B and/or spacer sections 136A, 136B, arranged end to end along the spine 120. Adjoining sleeve sections 131A, 131B, 136A, 136B may be mechanically engaged by being rotationally interlocked, e.g. by engaging the cogs 133 on each sleeve section, so that turning one sleeve section is effective to also turn the other sleeve sections. The tap sleeve 130 and proximal sleeve section 137 may also be rotationally interlocked by engaging cogs 133 on proximal sleeve section 137 with cogs 133 on sleeve section 136. The tap sleeve 130 and bit 110 may be rotationally interlocked by engaging cogs 133 on tap section 131A with cogs 113 on bit 110 as noted above. As a result, rotation of the proximal sleeve section 137 around longitudinal axis 150 of spine 120 may be effective to also rotate the tap sleeve 130 and the bit 110.

In general, with reference to FIG. 1, articulated bone tap apparatus 100 may comprise sleeve sections that are jointed to allow the apparatus 100 as a whole to bend into a curve. The sleeve sections may be jointed in such a way as to prevent relative axial rotation and transverse displacement, but to allow limited divergence from a straight line, whence, the apparatus 100 as a whole can assume a curved shape. The sleeve sections may for example be connected by universal joints similar to the ones used at the ends of truck drive shafts; may be joined by elastomer; or, the sleeve sections may include cogs or gear teeth, as in the illustrated embodiment, that mesh to prevent relative axial rotation and to prevent adjacent sleeve sections from becoming eccentric, while still allowing adjoining sleeve sections to have some angular difference between their respective axes. That is, the axes of adjoining sleeve sections intersect but are not necessarily parallel.

To control the bendability and/or curvature of the apparatus 100, embodiments may include a bendable spine such as spine 120, which may be made for example from metal wires or rods. Spine 120 may run through the center of the apparatus 100 in internal bores 134 of each sleeve section. The spine 120 may vary in diameter, cross section, or temper so as to have a bending stiffness that varies along the length of the apparatus 100 according to a predetermined function of distance from the proximal or distal end of spine 120, or the spine 120 diameter, cross section, or temper may be constant along the length of spine 120. The spine 120 may also have an external thread and/or a composite structure comprising multiple longitudinal spine sections 121A, 121B for guiding the apparatus 100, as described herein.

Figure 5:
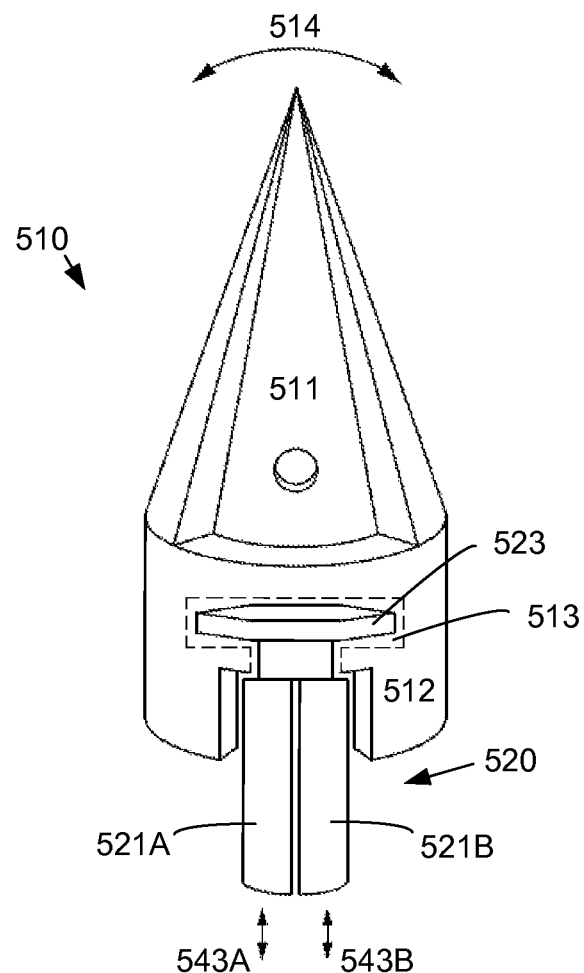
FIG. 5 is a diagram illustrating an example movable bit.
Figure 6:
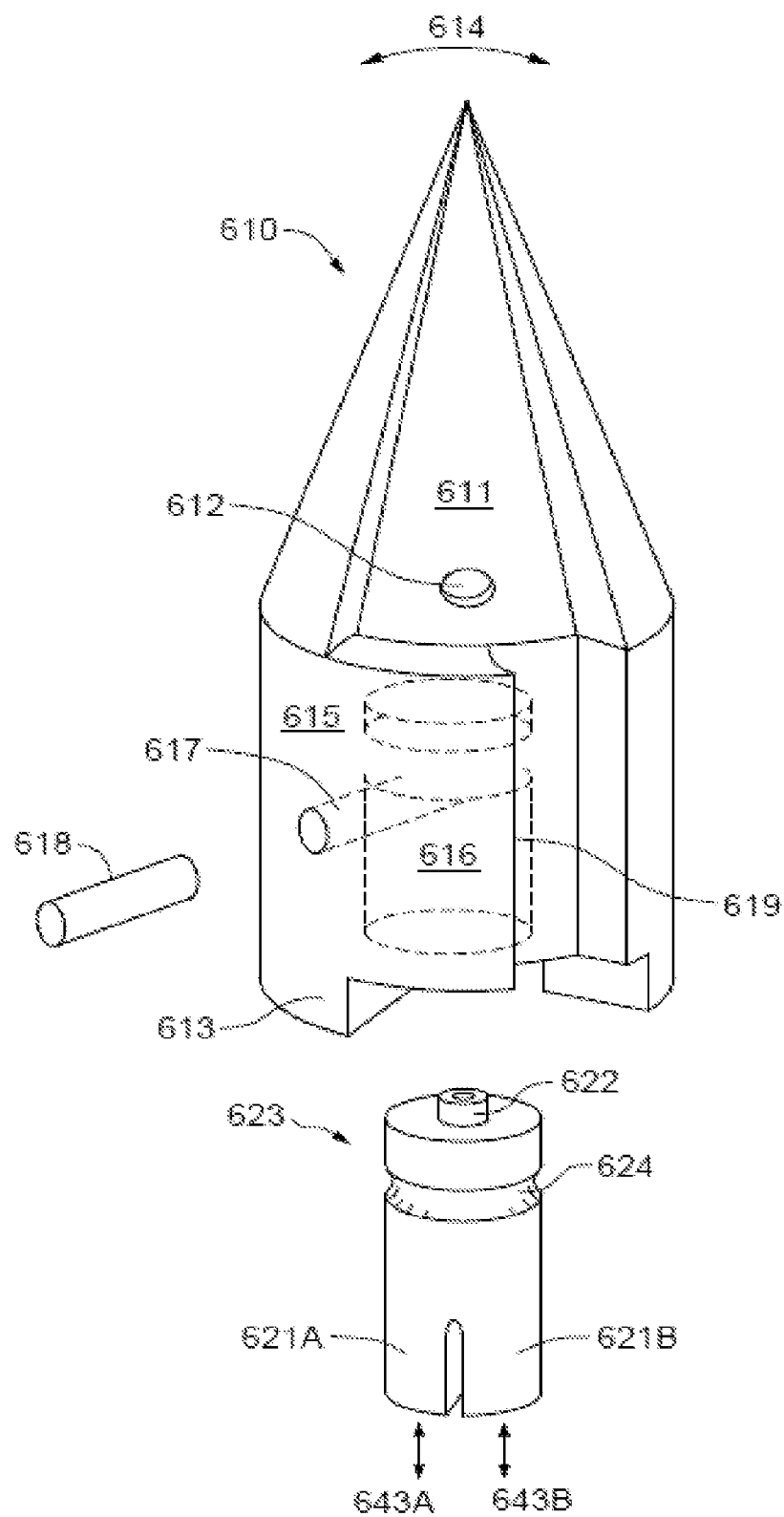
FIG. 6 is a diagram illustrating an example movable bit adapted to drill, mill in directions substantially perpendicular to a drill sleeve, and/or interchange with other bits.

In some embodiments, proximal sleeve section 137 may comprise a driver interface 138 adapted to couple with a driver to apply torque to the sleeve 130. A driver coupling with driver interface 138 may comprise, for example, a surgeon's wrench or powered driver that engages driver interface 138. Turning proximal sleeve section 137 may be effective to turn tap sleeve 130 and bit 110 as described above. Bit 110 may be rotatably attached to spine 120 so that the bit 110 rotates independently from the spine 120. FIG. 5 and FIG. 6 illustrate example movable bits that are adapted to rotate independently from the spine 120.

Bit 110 may comprise one or more cutting teeth 111A, 111B which may have cutting edges disposed thereon. Teeth 111A, 111B may be adapted to cut a hole into surrounding material as the bit 110 rotates, e.g., by shaving off a layer of bone in contact with teeth 111A, 111B. Cutting teeth 111A and 111B may be primarily adapted for forward cutting in the axial direction. As described in connection with FIG. 6, bits may additionally and/or instead comprise cutting edges (e.g., 619 in FIG. 6) that are primarily adapted to cutting laterally, e.g., for milling. Other shapes of bit 110, which are conventional or which include a combination of conventional cutting teeth and other features, are within the scope of this disclosure. The illustrated bit 110 is exemplary.

In some embodiments, cutting teeth 111A, 111B may have cutting edges disposed thereon to promote cutting into surrounding material when bit 110 rotates clockwise, counterclockwise, and/or in either sense, clockwise or counter-clockwise. Alternatively, cutting teeth 111A, 111B may be adapted for drilling in a conventional right-handed or clockwise cutting direction of rotation, or in a left-handed or counter-clockwise cutting direction of rotation. The bit 110 may have an interface adapted to couple with the distal end of the spine 120, for example, as illustrated in FIG. 5 and FIG. 6.

Tap sections 131A, 131B may each comprise external tap flutes 132 configured to cut a spiral groove into a sidewall of a hole cut by the bit 110 as the sleeve 130 rotates. In some embodiments, the height of the tap flutes 132 may increase with distance from the bit 110. For example, the height h1 of the tap flute 132 on tap section 131A may be shorter than the height h2 of the tap flute on tap section 131B, and the heights of tap flutes on any additional tap sections may likewise increase above the height h2 of the tap flute on tap section 131B. In some embodiments, tap flutes according to this disclosure may be arranged to be similar in some respects to the shape of flutes of conventional tap apparatus, and tap flutes according to this disclosure may generally apply a similar thread-cutting principle. However, unlike conventional tap apparatus, tap flutes according to this disclosure may be adapted on articulating sleeve sections. As a result, tap flutes according to this disclosure may have "missing" axial sections, and may have "missing" teeth as compared to conventional tap arrangements. To accommodate the "missing" sections, sequentially successive tap flutes may be separated by a distance equal to a multiple of the thread pitch, or may otherwise be aligned with a same spiral thread pitch line as other tap flutes.

Tap sections 131A, 131B as well as spacer sections 136A, 136B and proximal sleeve section 137 may comprise internal bores 134 configured to house spine 120. Adjoining sleeve sections 131A, 131B, 136A, 136B, and 137 may also be angularly adjustable to permit at least some degree of angular displacement between adjoining sleeve sections. Steering the bit 110 may result in a nonlinear or curved hole, and angular displacement between adjoining sleeve sections may allow bending of the sleeve 130 to accommodate curvature of the hole. In some embodiments, adjoining sleeve sections 131A, 131B, 136A, 136B, and 137 may be angularly adjustable by an appropriate shape of cogs 133, e.g., by using tapered cogs, as described with reference to FIG. 4.

Embodiments may include any of a variety of features adapted to flush material from holes in which articulated bone tap apparatus 100 is inserted. In some embodiments, bit 110 may comprise a sidewall hole 112 and spine 120 may include an internal conduit 122. Bit 110 may include an internal channel linking internal conduit 122 to sidewall hole 112. Saline solution or other sterile liquid pumped through internal conduit 122, e.g., from a section of internal conduit 122 extending through the steering nut 140, as shown, and the solution may exit bit 110 through sidewall hole 112 to flush any loose material surrounding cutting teeth 111A, 111B.

Figure 4:
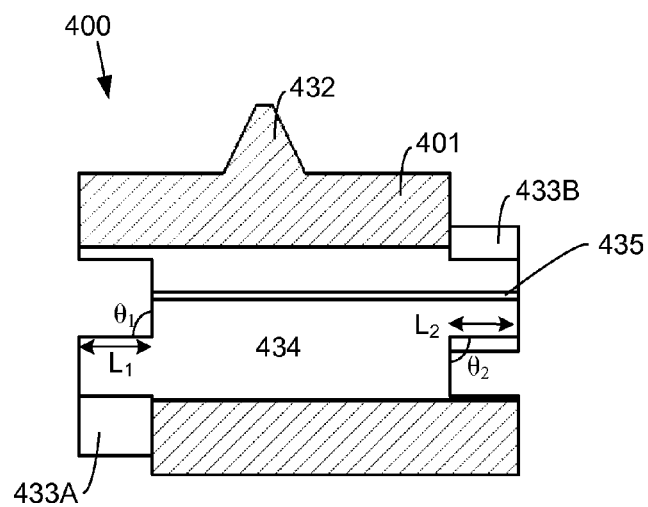
FIG. 4 is a diagram illustrating a cross sectional view of an example rigid cylindrical tap section for a tap sleeve.

Embodiments may furthermore be adapted to transmit fluids and material, such as saline solution pumped through sidewall hole 112 along with bone shavings, from the distal to the proximal end of the articulated bone tap apparatus 100. In some embodiments, the internal bores 134 of the sleeve sections 131A, 131B, 136A, 136B, and 137 may be of larger diameter than the spine 120, thereby providing an internal fluid conducting gap between the tap sleeve 130 and the spine 120. In some embodiments, the internal bores 134 of the sleeve sections 131A, 131B, 136A, 136B, and 137 may comprise longitudinal grooves, e.g., as illustrated in FIG. 4, thereby providing one or more internal fluid conducting grooves in the interior of the tap sleeve 130. External grooves on the outer surfaces of the sleeve sections 131A, 131B, 136A, 136B, and 137 may be provided in addition to or in place of longitudinal grooves. Such external grooves may function to draw material from the distal to the proximal end of the articulated bone tap apparatus 100 in a similar way as the helical grooves of a drill bit. Furthermore, in some embodiments, cogs 133 may be of different lengths to produce gaps between adjoining sleeve sections, allowing fluids and material to enter into the sleeve 130 and to be conducted back to the proximal end of the articulated bone tap apparatus 100.

In an example embodiment according to FIG. 1, a sequence of sleeve sections 131A, 131B, 136A, 136B, and 137 may be fitted over the spine 120. Each sleeve section may have at either end cogs 133 that intermesh, like gear teeth, with the cogs 133 of adjacent sleeve sections. Each of the cogs 133 may optionally be slightly tapered to allow angular deviation of the axes of adjacent sleeve sections when the sleeve sections are not tightly pressed together, but the tapered cogs 133 may tend to force the sleeve sections 131A, 131B, 136A, 136B, and 137 into axial alignment when the sleeve sections are compressed together. This can allow the surgeon to control the nonlinear trajectory of apparatus 100.

Each sleeve section 131A, 131B, 136A, 136B, and 137 may have a central axial bore 134, through which the spine 120 fits. Between the bore 134 and the spine 120 may be enough space to allow saline solution ejected from the sidewall holes 112 to pass along the tapped hole in the outward direction toward the incision, carrying bone chips with it. The space may be provided by a difference of diameter and/or by internal longitudinal grooves in the bore 134 (not shown in FIG. 1). Also, the cogs 133 at one end of each section may be longer than those at the other end, creating radial gaps to allow saline and/or bone chip fragments to pass radially inward to the bore 134, whence they can be washed away.

In some embodiments, the outer diameter of the main body of sleeve sections 131A, 131B, 136A, 136B, and 137 may be equal in diameter to the hole drilled by the bit 110. To provide threads in the bone which allow embodiments to grip the bone firmly, tap sections 131A, 131B may comprise tap flutes 132. Tap sections 131A, 131B, and/or further tap sections may be arranged in a sequence of graded radial heights of the tap flutes 132, and that the flutes of any one section may also be graded in radial height. The tap flutes 132 may thus gradually increase in diameter with axial distance from the tip of bit 110, and also with rotational angle about the axis 150, so that the peaks (i.e., the radially outermost surface) of the tap flutes 132 follow a conical helix. The gradation of tap flutes' 132 heights means that each tap flute may cut an additional thin shaving, beyond that cut by previous tap flute 132. In some embodiments, tap flutes according to this disclosure may be partly similar in shape, function, and use to flutes of conventional tap apparatus, but may be deployed differently to accommodate articulation of apparatus 100. In general, designs for tap flutes according to this disclosure may be obtained by cutting a conventional tap design into segments, and then further modifying those segments to resemble the sections of the sleeve 130, as illustrated.

At a certain axial distance from the bit 110, the threads will be complete, and at this point the tap flutes 132 can be replaced with sections having a solid male thread, or, with sections having no flutes, such as spacer sections 136A and 136B. At the far proximal end, the proximal sleeve section 137 can be shaped for turning with a surgeon's wrench or an automatic driver, for example by including wrench flats (driver interface) 138. Due to the cogs 133, torque applied at the proximal end will be transmitted to the more-proximal sections and finally to the bit 110.

The structure described above allows the tapping of a threaded hole from any point on the surface of a bone to any of various other points on the surface of the bone, by rotating the sleeve sections 131A, 131B, 136A, 136B, and 137 and bit 110, e.g., rotating alternately clockwise and counter-clockwise, and using irrigation and/or suction to remove chips generated by the cutting. The threaded hole so produced in a bone allows for compression of a fracture or dislocation as described herein.

Figure 2:
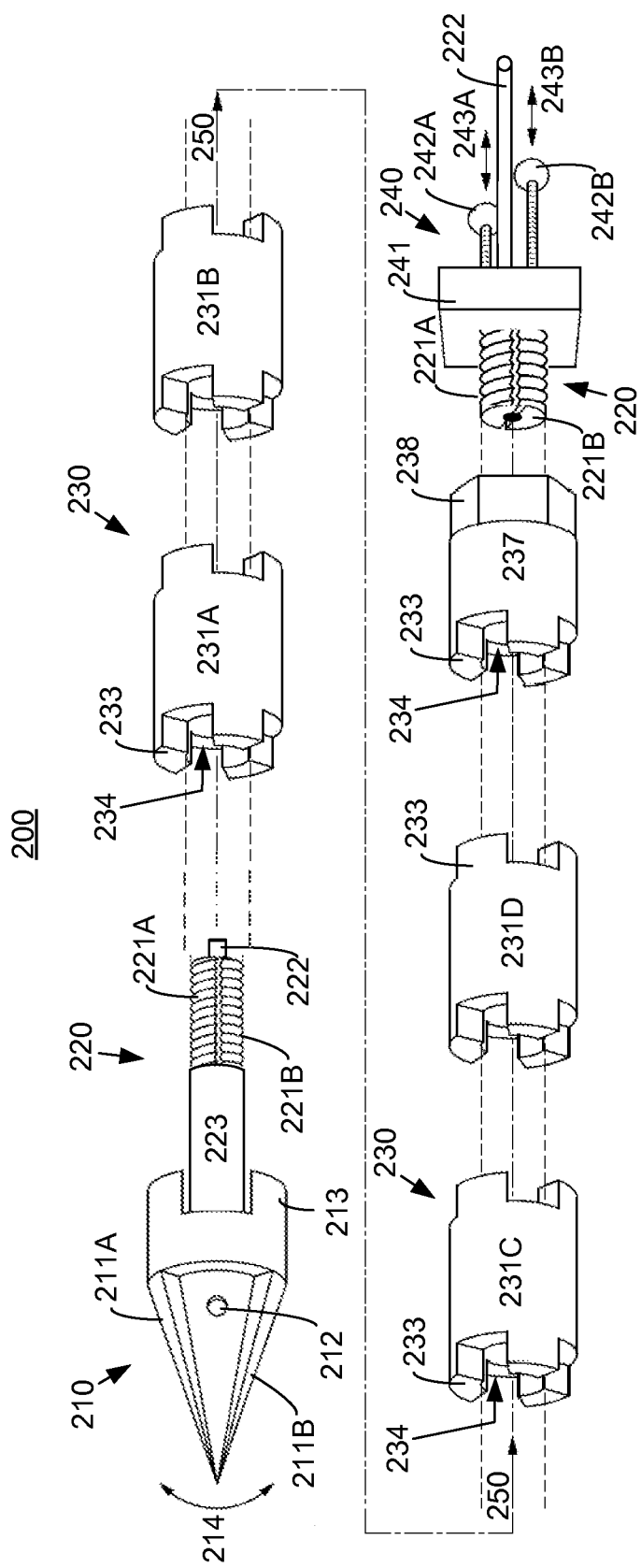
FIG. 2 is a diagram illustrating an exploded view of an example articulated bone drill apparatus.

FIG. 2 is a diagram illustrating an exploded view of an example articulated bone drill apparatus, arranged in accordance with at least some embodiments of the present disclosure. Example articulated bone drill apparatus 200 comprises a movable bit 210, a bendable spine 220, a flexible cylindrical drill sleeve 230, and a steering nut 240. Movable bit 210 comprises cutting teeth 211A, 211B, a sidewall hole 212, and cogs 213. Movable bit 210 is steerable by tensioning spine 220 and/or displacing spine sections 221A and 221B to adjust angle 214, as described with reference to FIG. 1. Spine 220 comprises head section 223, spine sections 221A and 221B, and internal conduit 222, having longitudinal axis 250. Drill sleeve 230 comprises rigid cylindrical drill sleeve sections 231A, 231B, 231C, 231D, and 237. Sleeve sections 231A, 231B, 231C, 231D, and 237 each have an internal bore 234 and cogs 233. Proximal sleeve section 237 has a driver interface 238. Steering nut 240 comprises base 241 and pulls 242A and 242B, which may be adjusted by adjustments 243A and 243B to displace spine section 221A with respect to spine section 221B.

Articulated bone drill apparatus 200 may contain various features generally described above in connection with articulated bone tap apparatus 100, and may generally be operable in similar fashion. Articulated bone drill apparatus 200 does not include tap sections having tap flutes. As a result, articulated bone drill apparatus 200 may produce a smooth-walled hole, not having a spiral groove in a sidewall thereof, such as produced by articulated bone tap apparatus 100. Articulated bone drill apparatus 200 may be used independently from articulated bone tap apparatus 100, or in some processes, articulated bone drill apparatus 200 may be used before or after using articulated bone tap apparatus 100 as described herein.

The various components of tap apparatus 100 and drill apparatus 200 may be made from any appropriate materials, whether now available or as may be developed. In general, appropriate materials for bits 110 and 210 and sleeve sections 131A, 131B, 136A, 136B, 137, 231A, 231B, 231C, 231D, and 237 may include conventional materials, such as stainless steel, titanium, or other metals, which are biocompatible and are also strong and/or hard enough to act as a cutting tool and/or fastener. In general, the materials already in use for surgical cutting tools such as drills; surgical fasteners; and surgical cutting/fastening devices such as bone screws, will be suitable for embodiments of this disclosure. Non-metallic materials, e.g., ceramic coatings, engineering plastics, and the like, may be used in some embodiments as appropriate, so long as they are of sufficient strength and hardness or can be combined with other materials so as to cut into bone. Spines 120 and 220 may be made of the same materials, so long as they are elastic; biocompatible spring steel would be suitable in some embodiments. Also, materials may differ depending on whether an embodiment is designed to be left in the body.

FIG. 3 is a diagram illustrating an example articulated bone tap or drill apparatus disposed in a bone, arranged in accordance with at least some embodiments of the present disclosure. Articulated bone tap or drill apparatus 300 may be configured according to FIG. 1 or FIG. 2. Apparatus 300 may comprise, inter alia, a bit 310, a flexible cylindrical sleeve 330 encasing a bendable spine, and a steering nut 340. A wrench 350 may be coupled with a proximal sleeve section, for use in applying a torque and/or turning the sleeve 330 and bit 310. An internal conduit 322 may extend from the proximal end of the apparatus 300 to the bit 310 at the distal end of the apparatus 300, and internal conduit 322 may optionally be coupled with a fluid pump (not shown) at the proximal end of the apparatus 300. Apparatus 300 is illustrated inside a first bone 360, wherein apparatus 300 enters first bone 360 through skin 320. First bone 360 comprises a bone fracture 363, a compact bone wall 361, and cancellous bone 362. A dislocated second bone 365 includes a compact bone wall 366 and cancellous bone 367.

In some embodiments, bone 360 may for example comprise a human hip bone, and a surgical access site where bone 360 meets skin 320 may comprise the ridge of the hip bone, which lies near the skin 320 surface and is generally easily accessible in patients, including the obese. This site is not close to important organs, and drilling there may cause minimal damage and minimal infection risk, because only a small incision in the skin 320 may be needed. Because the apparatus 300 traverses the inside of bone 360, there may be minimal danger of damage to nerves, blood vessels, or internal organs. In the case of fractures such as 363, the apparatus 300 may remain inside the bone 360 or protrude slightly; in the case of dislocations, apparatus 300 may traverse inter-bone spaces, e.g., between bones 360 and 365, which normally (without a dislocation) do not exist, and in which no organs are generally present, unless an accident has pushed organs into the gap, in which case an auxiliary incision over the gap between bones 360 and 365 can be made for additional access as necessary.

Apparatus 300 may be able to exert appreciable force to reduce and/or stabilize fractures such as 363 and dislocations, such as a dislocation of bones 360 and 365, either by exerting tension on the spine (e.g., spine 120 or 220) inside apparatus 300, or by removing the apparatus 300 and inserting threaded hardware, such as articulated screws or bolts, all of which can be inserted from a same incision in skin 320 that was used to insert the apparatus 300. Apparatus 300 may be able to exert such forces without necessarily applying mechanical devices at, and without necessarily requiring incision, at the point of the injury such as at fracture 363 or at the location of the dislocation of bones 360 and 365.

An example method of use of apparatus 300 will be discussed below, and methods employing apparatus 300 are further described in connection with FIG. 8. In an example use of apparatus 300, an entry point in skin 320 may be along the anterior superior iliac spine, the bony ridge of the hip bone, which is easily accessible because it is near the skin 320. Numerous tendons and ligaments attach along the ridge, but they exert forces lateral to the ridge, and therefore they extend away and are thinning or even absent at the crest of the ridge. This ridge extends along the hip and remains near skin 320 over a distance of many inches, from the groin to the back. Because it lies near the body's surface, because it is easily uncovered, and because it can be accessed without danger to any organs, the iliac spine is an ideal point for surgical entry.

In some examples, a surgeon may uncover the iliac spine at a chosen point in skin 320 and may then drill a hole into the interior of the hip bone 360, deep enough to reach the soft inner cancellous bone 362. The drilling direction may be parallel to a plane that is tangent to the interior bowl-shaped surface of the hip bone 360, although the drilling direction might be perpendicular to the surface of the iliac ridge at the entry point, that is, it might be perpendicular to a line tangent to the iliac ridge. This initial drilling operation may be done with an ordinary straight bone drill, or optionally with a drilling apparatus such as apparatus 200. The drilled hole may optionally be of wider diameter than the outer edges of the widest tap flutes 132, to allow easy insertion of apparatus 100. Appropriate selection of a drilling direction may insure that the bit 310, when inserted into the drilled hole, enters the inner cancellous bone 362 and the trajectory of apparatus 300 lies between the two layers of compact bone 361. A tangent plane may be selected to point apparatus 300 in the direction of the fracture 363 or dislocation to be mended.

If the surgeon continued drilling in the initial entry direction with an ordinary straight bit, the bit would emerge from the posterior surface of the hip bone 360, which is bowl shaped. In embodiments using apparatus 300, the surgeon may stop drilling once the inner cancellous bone 362 is reached and may then insert the apparatus 300 into the drilled hole. The surgeon may then begin drilling or tapping by rotating the apparatus 300 alternately in both senses of direction but, in the application of tap apparatus 100, turning more in the forward direction.

The apparatus 300 may be adapted to traverse the softer cancellous bone 362 between the harder outer layers of compact bone 361, burrowing like a worm between two plates, to a chosen point. The apparatus 300 may follow the inner surface of the compact bone 361 because the compact bone 361, being hard, will deflect the apparatus 300 into the softer cancellous bone 362. The apparatus 300, following the path of least resistance, will burrow through the bone 360 from the right to the left side illustrated in FIG. 3.

Thus, if started in the right direction by the preliminary drilled hole, the apparatus 300 may travel to a point that is tolerably near to a desired exit point from bone 360, even if that exit point is some distance away from the entry point, and even without active guidance of the bit 310. Active guidance of the non-linear path can be provided, e.g., by manipulating a two- or three-part spine, the sections of which may be relatively compressed or stretched to affect the spine's curvature and thereby steer the bit 310.

Once the apparatus 300 reaches a second compact bone wall at the left side of bone 360, for example where bone 360 meets the pubic symphysis or the sacroiliac joint, apparatus 300 may be surrounded by compact bone on three sides, instead of two. Due to its limited flexibility, apparatus 300 may not be deflected from the second compact bone wall, but may cut into the second compact bone wall, and may optionally emerge from bone 360 on the left side thereof as illustrated in FIG. 3. The apparatus 300 may then enter dislocated bone 365, e.g., apparatus 300 may bridge the pubic symphysis, or may exit the ilium and begin to burrow into the sacrum.

If a dislocated joint has been rearranged to its correct juxtaposition by closed reduction, that is, by manipulation, through unbroken skin, that temporarily corrects a dislocation, then the bit 310 and the sleeve sections may continue across the gap between bones 360 and 365 and may drill and/or tap into the dislocated bone 365. After apparatus 300 penetrates deeply enough into the dislocated bone 365, the two bones 360 and 365 can be locked together by the apparatus 300, especially when apparatus is a tap apparatus 100, as the tap flutes 132 will firmly grip the bones 360 and 365. Apparatus 300 can be fixed in compression by exerting tension on the spine, for example by turning a split nut or a conventional nut on a protruding threaded portion of the spine 120 or 220, so that the sleeve sections act much as a screw would, and hold the two bones 360 and 365 together.

The joint between the hip bone and the sacroiliac is a lap joint. Some embodiments may be adapted for use in connection with lap joints, to avoid the possibility of apparatus 300 emerging from bone 360 into soft tissue, rather than into bone 365, such as the sacrum. To treat the lap joint at the sacroiliac, as well as other lap joints, embodiments may be adapted to cut into compact bone 361 on either side of the cancellous bone 362 at the discretion of the surgeon, e.g., before reaching the far left side of bone 360 in FIG. 3, which is a place where apparatus 300 is effectively forced to cut into compact bone 361 by the pelvic-bone geometry. Embodiments may be adapted for use in connection with dislocated lap joints by, inter alia, employing a bit which is adapted to drill in directions substantially perpendicular to the drill sleeve, e.g., as illustrated for example by bit 610 in FIG. 6, and a two-stage operation of drilling followed by tapping, or "pre-drilling" as described for example in connection with FIG. 8. This two-stage operation (for example, using the device of FIG. 2 followed by using the device of FIG. 1) may also be used when there is no milling or lateral drilling in directions substantially perpendicular to the drill sleeve.

Using a drill apparatus 200 as the apparatus 300 in FIG. 3, with a lateral drilling bit or milling cutter, or a combination bit such as 610 as illustrated in FIG. 6 which includes lateral cutting edges 619 on its cylindrical base portion, and may be adapted for both forward and lateral cutting, allows the surgeon to drill laterally into compact bone 361 at any desired location, such that the bit 610 can exit the bone 360 at any chosen location. The absence of tap flutes 132 allows drill apparatus 200 to engage compact bone 361 without continually progressing forward.

When pre-drilling into compact bone 361 with an apparatus 200 equipped with a lateral drilling bit 610, the surgeon may guide the bit 610 through the pelvic bone (for example, starting at the most anterior point of the iliac) to a point near the sacrum, where the bit 610 can be made to exit the pelvic bone, e.g., bone 360, on a side adjacent to the sacrum. In this way, the trajectory of apparatus 200 can be made to aim right for the sacrum (or the point where the sacrum should be, if the joint is separated). Then, the drilled hole can be continued into the sacrum (bone 365 in FIG. 3) at a desired location and afterwards, the drill apparatus 200 can be withdrawn and the tap apparatus 100 may be used to thread drilled holes in the bones 360 and 365. Once the holes in the two bones 360 and 365 are threaded, the tap apparatus 100 can be withdrawn and a screw or other hardware may be used to join bones 360 and 365 together. The screw may be short and/or articulated to allow for travel through bone 360 and engagement of the tapped threads.

The tap apparatus 100 can be left in position for any amount of time, or may be removed and replaced with an articulated screw having a same thread as that cut by the tap apparatus 100. There are several reasons why this might be done: (1) the sharp edges of the tap flutes 132 and bit 110 might cause pain, before being thoroughly grown over with bone; (2) the tap apparatus 100 can be re-used after thorough sterilization; and (3) the screw may be stronger than the tap apparatus 100. If the tap apparatus 100 is to be left in place for a matter of days, it might be rotated slightly at intervals to prevent bone growth from later preventing easy withdrawal.

In curved tapped holes produced by tap apparatus 100, the spiral thread groove may have different pitch on the inside and the outside of the curve. However, each tap section 131A and 131B may be sufficiently short in length to minimize interference over the axial length of each tap section 131A and 131B. Any screw which takes the place of the tap apparatus 100 may also to be articulated for this reason; a very long rigid screw section may jam or damage the spiral thread groove cut by the tap apparatus 100, unless the tapped hole through the bone 360 happens to be straight.

When treating individual broken bones, tap apparatus 100 may be deployed to exert a compressive force across a fracture 363. For example, if the ischium is fractured, tap apparatus 100 can bridge across the fracture 363 and press the two sides of the fracture 363 together. In some embodiments, tap apparatus 100 may be removed from bone 360, and a screw can be inserted through the hole from the iliac ridge and threaded into the hole on the far side of the fracture 363, e.g. at a tapped hole on the left side of bone 360, and another screw can be threaded to the iliac ridge at the right side of bone 360; then these two screws can be connected by a tensile member to exert a compressive force on the fracture 363, stabilizing the fracture 363. Also, in some embodiments, "self-tapping" sleeve sections or bone screws might be used for firm seating in the second compact bone wall.

In another example, a break in the front portion of a jaw bone may be treated through an incision made behind the jaw; or, a fracture of the femur might be put into traction by drilling into the trochanter major (upper end of the thighbone) and then tapping into the portion of the femur beyond the break. A bone repair in which no curvature of apparatus 100 is needed, such as certain types of femur repair, may be performed with drills and taps which are not articulated, as well as with the articulated tools illustrated. As mentioned above, in some embodiments the flexibility of apparatus 100 can be decreased by tensioning the spine, and this may allow embodiments of this disclosure to be used in the manner of non-articulated straight taps. Embodiments may include methods of exerting traction on a broken bone by tapping into one portion and exerting force on the other portion, using threaded elements such as a threaded rod screwed into the distal bone and a nut screwed onto the outside surface of the proximal bone. In a long bone such as the femur, embodiments may have the advantage that the greater length of thread engagement provides greater holding power, so that the apparatus can be of smaller diameter and therefore less invasive, as compared to conventional surgery.

When treating dislocated joints, in some embodiments, joints may be gradually brought together by turning tap apparatus 100, or by turning an articulated screw inserted after removal of tap apparatus 100. For example, tap apparatus 100 may be withdrawn from the dislocated second bone 365, and then re-engaged with threads tapped in the dislocated second bone 365, but one thread closer than previously, drawing bones 360 and 365 together. Also, two bones of a dislocated joint can be pulled together by tapping into the bone which is more distal from the incision (such as bone 365 in FIG. 3), threading a screw into the more distal bone, and then exerting a force pulling the two bones together, by pulling on a flexible element attached to the screw, from the point of incision. Such methods do not require tapping the more proximal bone (such as 360 in FIG. 3) and can be done by first drilling, using apparatus 200 illustrated in FIG. 2, followed by tapping using the apparatus 100 as in FIG. 1, and finally drilling the first bone to a larger diameter using a drill of larger diameter (or, by drilling the first bone to the larger diameter first, and finally tapping the second bone). Such methods may allow an articulated screw, having a major diameter corresponding to the larger diameter mentioned above, to be easily inserted up to the second bone and then rotated to tighten the screw.

Embodiments may be used to drill or tap holes and/or insert stabilizing threaded screws or other hardware almost anywhere in the pelvic ring and also to exert stabilizing or corrective forces between bones or within a bone, while avoiding large incisions and interference with vital organs. For most places in the pelvic ring, there is a relatively straight trajectory to that place from the iliac ridge. For example, in some embodiments an apparatus 300 may run from the very front of the iliac ridge straight back to the sacroiliac joint, or from above the hip joint down to the pubic symphysis or the ischium.

FIG. 4 is a diagram illustrating a cross sectional view of an example rigid cylindrical tap section for a tap sleeve, arranged in accordance with at least some embodiments of the present disclosure. An example tap section 400 may include a cylindrical section body 401 which defines an internal bore 434. Internal bore 434 may comprise one or more longitudinal grooves such as longitudinal groove 435. Cogs 433A and 433B may extend from the ends of the cylindrical section body 401. Other sleeve sections such as spacer sections 136A, 136B, proximal sleeve section 137, and corresponding drill sleeve sections such as 231A, 231B, 231C, 231D, and 237 may similarly comprise a body 401, bore 434, grooves 435, and cogs 433A, 433B. Tap section 400 may furthermore comprise an external tap flute 432 extending from an external sidewall of the cylindrical section body 401.

Cogs 433A and 433B may have lengths $L_1$ and $L_2$, respectively. $L_1$ and $L_2$ may optionally be different to allow for spaces between sleeve sections, as described herein. Also, cogs 433A and 433B may meet cylindrical section body 401 at angles $\theta_1$ and $\theta_2$, respectively. In some embodiments, $\theta_1$ and $\theta_2$ may be greater than 90 degrees to provide a tapered shape to cogs 433A and 433B, as described herein.

FIG. 5 is a diagram illustrating an example movable bit, arranged in accordance with at least some embodiments of the present disclosure. Bits according to FIG. 5 may be used in place of bit 110 in FIG. 1, bit 210 in FIG. 2, and/or bit 310 in FIG. 3 in some embodiments. An example moveable bit 510 may include a bit tip 511 and a bit base 512. Bit base 512 may be adapted to couple with a bendable spine 520 effective to allow steering the bit tip 511 to a desired angle 514. For example, bit base 512 may include a cavity 513 adapted to receive an anchor 523, fitting in the cavity 513 with sufficiently small clearance that the bit 510 can rotate relative to the spine 520 but remains substantially axially aligned with the spine 520 during such rotation. Anchor 523 may be coupled with spine sections 521A, 521B. Spine sections 521A, 521B may be displaced by adjustment forces 543A, 543B to adjust an angle of anchor 523, and thereby adjust angle 514.

In some embodiments, cavity 513 may be adapted with a shape and size substantially similar to that of anchor 523, or slightly larger than anchor 523. When a sleeve that is mechanically engaged with bit 510 rotates, cavity 513 may rotate around anchor 523. In some embodiments, ball bearings may be included in cavity 513 between anchor 523 and the walls of cavity to facilitate rotation of bit 510. When an angle of anchor 523 is adjusted by adjustments 543A and 543B, anchor 523 may apply pressure on diagonally opposite top and bottom walls of cavity 513 to adjust angle 514.

FIG. 6 is a diagram illustrating an example movable bit, arranged in accordance with at least some embodiments of the present disclosure. Bits according to FIG. 6 may be used in place of bit 110 in FIG. 1, bit 210 in FIG. 2, and/or bit 310 in FIG. 3 in some embodiments. An example moveable bit 610 may include a bit tip 611 and a bit base 615. Bit tip 611 may include a sidewall hole 612 and cutting teeth, similar to the bit tips illustrated in FIG. 1 and FIG. 2, respectively. Bit base 615 may comprise cogs 613 similar to cogs 113 and 213, a cutting edge 619 adapted to mill laterally or otherwise cut in directions substantially perpendicular to a sleeve, spine, or bit 610, and an interface such as cylindrical cavity 616 adapted to couple with a bendable spine head section 623.

In some embodiments, bits including cutting edge 619 may draw from features adapted for milling machines, routers, and other apparatus known in the art or as may be developed. Bit 610 comprises a combination of a forward-cutting drill bit tip 611 and a side-cutting router or milling machine bit with cutting edge 619. Alternative embodiments may provide a purely forward-drilling bit, e.g., a bit 610 without cutting edge 619, or a purely milling cutter, e.g., a bit 610 without bit tip 611.

An interface such as cylindrical cavity 616 may be adapted to couple with a bendable spine head section 623, e.g. by being of a diameter equal to or slightly larger than the diameter of head section 623. In the illustrated example embodiment, cylindrical cavity 616 furthermore includes a pin hole 617 adapted for inserting a pin 618 through the bit base 615 into cylindrical cavity 616. Pin 618 may axially secure head section 623 within cylindrical cavity 616 of the bit 610, while also allowing rotation of head section 623 (and therefore of the spine) with respect to bit 610. For example, pin 618 may enter cavity 616 along a cavity sidewall, at a location within cavity 616 matching a location of an annular groove 624 in head section 623. Pin 618 may be removed to allow insertion (or removal) of head section 623 in cavity 616 and pin 618 may be inserted to axially secure head section 623 within bit 610. Those of skill in the art will appreciate that other means for securing a spine within a bit, while simultaneously allowing rotation of the bit with respect to the spine, may be appropriate for some embodiments.

Embodiments according to FIG. 6 allow for interchanging different bits for use with an apparatus 100 or 200. For example, a bit 610 such as illustrated in FIG. 6 may be removed by removing pin 618, and bit 610 may be replaced by a purely forward drilling, or purely milling or side-cutting type bit. Furthermore, similar to the arrangement illustrated in FIG. 5, bit base 615 may be adapted to couple with the bendable spine head section 623 effective to allow steering the bit 610 to a desired angle 614. For example, spine sections 621A, 621B may be displaced by adjustment forces 643A, 643B to adjust an angle of head section 623, and thereby adjust angle 614.

FIG. 5 and FIG. 6 illustrate example bits in accordance with some embodiments of this disclosure. Those of skill with drill apparatus will appreciate that the example embodiments may be modified or other arrangements may be substituted. In the case of bits adapted for lateral drilling or milling as illustrated in FIG. 6, embodiments may draw from features adapted for milling machines, routers, and other apparatus known in the art or as may be developed.

FIG. 7 is a diagram illustrating a perspective view of one half of an example split nut adapted for use as a steering nut, arranged in accordance with at least some embodiments of the present disclosure. The example split nut 700 may comprise two or more sections such as 701, where, in embodiments comprising two half-sections, a second half section (not shown) may fit over the illustrated first half section 701. Split nut 700 may be split across a plane in which lies the axis of the spine 720 or of an apparatus such axis 150 or 250, so that each section of split nut 700 engages one of the spine sections 121A, 121B, which are, in this embodiment, externally threaded in the regions where the split nut 700 engages them. The sections such as 701 of the split nut 700 may be radially coupled but may be relatively movable in the axial direction by any suitable coupling mechanism. The split nut 700 may also be able to rotate as a whole about its common axis with the spine 720, or, split nut 700 may include a mechanism for turning the spine 720 when the split nut 700 is rotated.

When the split nut 700 is rotated to a position where each half (or other fraction) such as 701 covers a respective section 721A or 721B of the spine 720, then the apparatus incorporating split nut 700 can be steered by exerting a force on each axially movable half 701 of the split nut 700, which may exert a push or pull on its respective spine section 721A or 721B by means of internal threads mating with the threads of the spine sections 721A or 721B. A difference in axial force applied to the spine sections 721A or 721B at the split nut 700, e.g., using means such as pulls or levers coupled with each section 701 of the split nut 700, may be communicated through the spine 720 to the bit, e.g., bit 110, creating a lateral force and also a torque tending to turn bit 110 to a desired angle 114. The torques and the lateral force at the bit 110 arise because the spine 720 is confined within the sections of the sleeve, e.g., sleeve 130, as described herein, so that the spine sections 721A, 721B slide over each other rather than separate from one another. At the same time that it tends to bend the spine 720, the split nut 700 can also exert an overall tensioning force on the spine 720, so as to change the flexibility of the apparatus as mentioned herein, by rotating the split nut 700, even while the tensioning or steering force is present, if the offset threads of the two halves such as 701 of the split nut 700 are aligned such that together they present a continuous internal thread. The split nut 700 may thus have more function than the pull-type steering nut embodiment illustrated in FIG. 1. In general, any mechanism that creates a difference in tension/compression or axial force between the two (or more) spine sections 721A, 721B can act to steer the bit 110, and thereby allow lateral cutting of bone, in some embodiments. Any mechanism that changes the total tension in the spine 720 can also be used.

Figure 8:
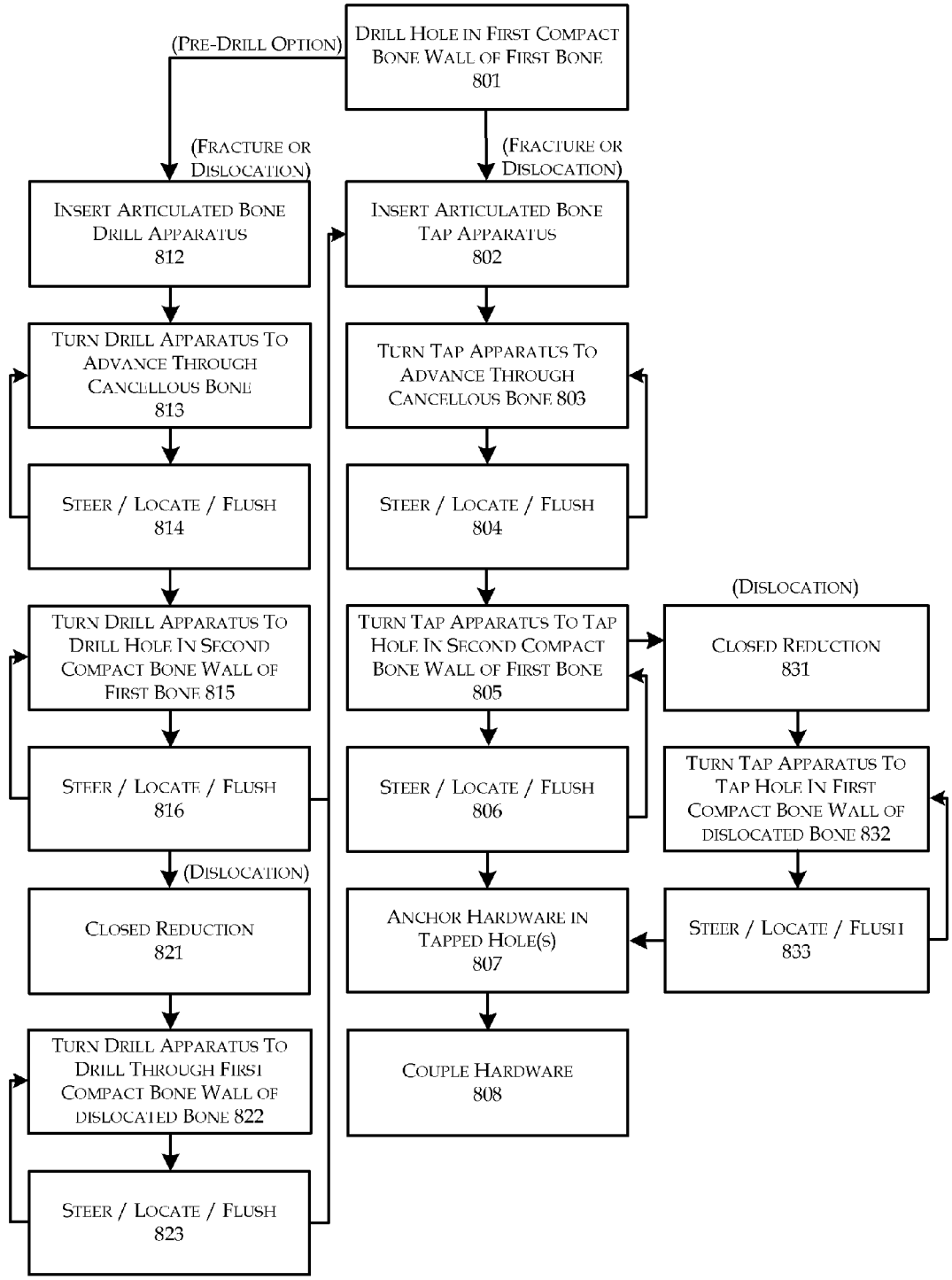
FIG. 8 is a flow diagram illustrating an example method for treating a bone fracture or dislocation, all arranged in accordance with at least some embodiments of the present disclosure.

FIG. 8 is a flow diagram illustrating example methods for treating a bone fracture and/or dislocation, arranged in accordance with at least some embodiments of the present disclosure. The example flow diagram may include one or more operations as illustrated by blocks 801-808, 812-816, 821-823, and 831-832. FIG. 8 includes blocks that are illustrated as being performed sequentially. It will be appreciated however that these blocks may be re-arranged as convenient to suit particular embodiments and that these blocks or portions thereof may be performed concurrently in some embodiments. It will also be appreciated that in some examples various blocks may be eliminated, divided into additional blocks, and/or combined with other blocks.

FIG. 8 illustrates example methods for treating a bone fracture and/or dislocation. In general, blocks 801-808 may optionally be combined with blocks 812-816 to treat bone fractures. Blocks 801-808, optionally combined with blocks 812-816, may be further combined with blocks 821-823 and/or blocks 831-832 to treat dislocations. Methods according to FIG. 8 may generally be understood by reference FIG. 3, which illustrates an example fracture 363 and dislocated bones 360 and 365.

At a "Drill Hole In First Compact Bone Wall Of First Bone" block 801, apparatus 300, or a standard bone drill apparatus, may be used to drill a hole in a first compact bone wall of a first bone 360. For example, apparatus 300 may be used to drill a hole in the portion of compact bone wall 361 at the far right side of FIG. 3. This portion of compact bone wall 361 is considered herein to comprise a "first compact bone wall" because it is situated at a first side of bone 360. Block 801 may be followed by block 812 when appropriate to employ pre-drilling operations, or block 801 may be followed by block 802 when no pre-drilling is necessary.

At an "Insert Articulated Bone Drill Apparatus" block 812, an articulated bone drill apparatus 200 such as illustrated in FIG. 2 may be initially used as apparatus 300 in FIG. 3. The articulated bone drill apparatus 200 may be inserted in the hole in the first compact bone wall formed at block 801. Block 812 may be followed by block 813.

At a "Turn Drill Apparatus To Advance Through Cancellous Bone" block 813, the articulated bone drill apparatus 200 inserted at block 812 may be turned using driver 350 to advance apparatus 200 through a non-linear path within cancellous bone 362 in the first bone 360 to a second compact bone wall of the first bone 360. An example non-linear path is illustrated in FIG. 3, wherein the apparatus travels through bone 360 in a path that is not a straight line. Apparatus 200 may be used to drill a hole in the non-linear path within cancellous bone 362 to the portion of compact bone wall 361 at the left side of bone 360 in FIG. 3. This left-side portion of compact bone wall 361 is considered herein to comprise a "second compact bone wall" because it is situated at a side of bone 360 other than the side associated with the first compact bone wall at the far right side of bone 360. Block 813 may be followed by block 814.

At a "Steer/Locate/Flush" block 814, any of a variety of operations may be performed, either continuously or intermittently, as apparatus 200 is advanced through bone pursuant to block 813. An arrow from block 814 to block 813 indicates that blocks 813 and 814 may be performed in a continuous loop, with as many cycles as necessary, as may be appropriate to advance apparatus 200. Block 814 may comprise one or more of a steering operation, a locating operation, or a flush operation. In an example steering operation, the articulated bone drill apparatus 200 may be steered by adjusting longitudinal displacement of spine sections within the apparatus 200 to direct the non-linear path of the apparatus 200 as the apparatus 200 advances within the cancellous bone 362 within bone 360. In an example locating operation, a location of the apparatus 200 within bone 360 may be established using one or more of an ultrasound, X-Ray, or nuclear medicine imaging technique. In an example flushing operation, the apparatus 200 may be flushed, e.g., by injecting fluid at internal conduit 322.

In an example locating operation using an ultrasound imaging technique, ultrasound produced by an ultrasonic transducer may be directed through the internal conduit 222 of the spine 220 and/or through the bore 234 of the sleeve sections, which ultrasound may escape through the sidewall holes 212, or through other portions of apparatus 200 and radiate out through the body. This approach enables the bit 210 to be located with ultrasonic sensors. Ultrasonic sensors might be placed on the outside of the body to pick up sound coming through the bone 360, or, they might be placed on the ridge of the bone 360 and use sonic delay to locate the source, at the bit 210. Alternatively, needles with sonic-probe tips may be inserted through the body to make direct contact with bones such as 360 and 365. Ultrasound imaging may be combined with and/or supplement other locating methods such as fluoroscopy. Some example methods may use a radioactive bit 210, and may locate the bit 210 for example by imaging emitted gamma rays. Blocks 813 and 814 may be followed by block 815.

At a "Turn Drill Apparatus To Drill Hole In Second Compact Bone Wall Of First Bone" block 815, the articulated bone drill apparatus 200 inserted at block 812 and advanced through cancellous bone 362 at block 813 may be turned using driver 350 to drill a hole in the second compact bone wall of the first bone 360, that is, to drill a hole in the portion of compact bone wall 361 at the left side of bone 360 in FIG. 3. Block 815 may be followed by block 816.

At a "Steer/Locate/Flush" block 816, any of a variety of operations may be performed, either continuously or intermittently, as apparatus 200 drills a hole in the second compact bone wall of the first bone 360 pursuant to block 815. An arrow from block 816 to block 815 indicates that blocks 815 and 816 may be performed in a continuous loop, with as many cycles as necessary, as may be appropriate to drill a hole using apparatus 200. Operations in block 816 may comprise steering, locating, and/or flushing operations described herein. To treat a fracture 363, blocks 815 and 816 may be followed by removing apparatus 200 from bone 360 and proceeding to block 802, without performing blocks 821-823 or 831-833. To treat a dislocation, methods need not (yet) remove apparatus 200 from bone 360, and may proceed from blocks 815 and 816 to block 821.

At a "Closed Reduction" block 821, a closed reduction operation may be performed to position dislocated bone 365 at a desired position and orientation with respect to first bone 360. For example, for ball and socket type joints, a ball or socket in bone 660 may be reduced to a position either over or inside a corresponding ball or socket at bone 365. For lap type joints, an overlapping bone section of bone 360 may be reduced to a position either over or under a corresponding overlapping bone section of bone 365. Block 821 may use any reduction technique known in the art. Block 821 may be followed by block 822.

At a "Turn Drill Apparatus To Drill Through First Compact Bone Wall Of Dislocated Bone" block 822, the articulated bone drill apparatus 200 inserted at block 812, advanced through cancellous bone 362 at block 813, and which drilled through the second compact bone wall of bone 360 at block 815, may be turned using driver 350 to drill a hole in a first compact bone wall of the dislocated bone 365, for example, to drill a hole in the portion of compact bone wall 366 at the right side of bone 365 in FIG. 3. Block 822 may be followed by block 823.

At a "Steer/Locate/Flush" block 823, any of a variety of operations may be performed, either continuously or intermittently, as apparatus 200 drills a hole in the first compact bone wall of the dislocated second bone 365 pursuant to block 822. An arrow from block 823 to block 822 indicates that blocks 822 and 823 may be performed in a continuous loop, with as many cycles as necessary, as may be appropriate to drill a hole using apparatus 200. Operations in block 823 may comprise steering, locating, and/or flushing operations described herein. Blocks 822 and 823 may be followed by removing apparatus 200 from bones 365 and 360, and proceeding to block 802.

At an "Insert Articulated Bone Tap Apparatus" block 802, an articulated bone tap apparatus 100 such as illustrated in FIG. 1 may be used as apparatus 300 in FIG. 3. The articulated bone tap apparatus 100 may be inserted in the hole in the first compact bone wall formed at block 801. Block 802 may be followed by block 803.

At a "Turn Tap Apparatus To Advance Through Cancellous Bone" block 803, the articulated bone tap apparatus 100 inserted at block 802 may be turned using driver 350 to advance apparatus 100 through a non-linear path within cancellous bone 362 in the first bone 360 to a second compact bone wall of the first bone 360. As noted herein, an example non-linear path is illustrated in FIG. 3, wherein the apparatus travels through bone 360 in a path that is not a straight line. Apparatus 100 may be advanced within cancellous bone 362 to the second compact bone wall at the left side of bone 360 in FIG. 3. In processes employing blocks 812-816, apparatus 100 may advance through a non-linear path that was pre-drilled by apparatus 200. In processes not employing blocks 812-816, apparatus 100 may advance through a non-linear path that was not pre-drilled. Block 803 may be followed by block 804.

At a "Steer/Locate/Flush" block 804, any of a variety of operations may be performed, either continuously or intermittently, as apparatus 100 is advanced through bone pursuant to block 803. An arrow from block 804 to block 803 indicates that blocks 803 and 804 may be performed in a continuous loop, with as many cycles as necessary, as may be appropriate to advance apparatus 100. Operations at block 804 may comprise steering, locating, and/or flushing operations described herein. Blocks 803 and 804 may be followed by block 805.

At a "Turn Tap Apparatus To Tap Hole In Second Compact Bone Wall Of First Bone" block 805, the articulated bone tap apparatus 100 inserted at block 802 and advanced at blocks 803-804 may be turned using driver 350 to advance apparatus 100 through the second compact bone wall of the first bone 360, that is, to advance apparatus 100 through the portion of compact bone wall 361 at the left side of bone 360 in FIG. 3. As it advances through the second compact bone wall of the first bone 360, apparatus 100 may tap the hole through which it advances, e.g., by tap flutes 132 cutting a spiral thread groove in a sidewall of the hole in the second compact bone wall of the first bone 360.

At a "Steer/Locate/Flush" block 806, any of a variety of operations may be performed, either continuously or intermittently, as apparatus 100 is advanced through bone pursuant to block 805. An arrow from block 806 to block 805 indicates that blocks 805 and 806 may be performed in a continuous loop, with as many cycles as necessary, as may be appropriate to advance apparatus 100. Operations at block 806 may comprise steering, locating, and/or flushing operations described herein. To treat a fracture 363, blocks 805 and 806 may be followed by block 807, without performing blocks 821-823 or 831-833. To treat a dislocation, blocks 805 and 806 may be followed by block 831.

At a "Closed Reduction" block 831, a closed reduction operation may be performed to position dislocated bone 365 at a desired position and orientation with respect to first bone 360, as described with reference to block 821. Block 831 may be followed by block 832.

At a "Turn Tap Apparatus To Tap Hole In First Compact Bone Wall Of Dislocated Bone" block 832, the articulated bone tap apparatus 100 inserted at block 802, advanced through bone 360 at blocks 803-806, may be turned using driver 350 to tap a hole in a first compact bone wall of the dislocated bone 365, for example, to tap a hole in the portion of compact bone wall 366 at the right side of bone 365 in FIG. 3. In processes employing blocks 821-823, apparatus 100 may advance through a pre-drilled hole in the first compact bone wall of the dislocated bone 365, e.g., the hole drilled using apparatus 200. In processes not employing blocks 821-823, apparatus 100 may be used to drill and tap the hole in the first compact bone wall of the dislocated bone 365. As it advances through the first compact bone wall of the dislocated bone 365, apparatus 100 may tap the hole through which it advances, e.g., by tap flutes 132 cutting a spiral thread groove in a sidewall of the hole in the first compact bone wall of the dislocated bone 365. Block 832 may be followed by block 833.

At a "Steer/Locate/Flush" block 833, any of a variety of operations may be performed, either continuously or intermittently, as apparatus 100 taps a hole in a first compact bone wall of the dislocated bone 365 pursuant to block 832. An arrow from block 832 to block 833 indicates that blocks 832 and 833 may be performed in a continuous loop, with as many cycles as necessary, as may be appropriate to tap a hole using apparatus 100. Operations in block 833 may comprise steering, locating, and/or flushing operations described herein. Blocks 832 and 833 may be followed block 807.

At an "Anchor Hardware In Tapped Hole" block 807, hardware may be anchored in holes tapped in either or both of the first compact bone wall of the dislocated bone 365, tapped at block 832, and/or the second compact bone wall of the first bone 360, tapped at block 805. In some embodiments, hardware may also be anchored in hole(s) tapped in the first compact bone wall of the first bone 360. For example, hardware adapted to exerting tension on a flexible member such as the spine 120 or 220 may be anchored a hole tapped in the first compact bone wall of the first bone 360. The flexible member may have threads engaged with the hardware anchored in the first compact bone wall of the first bone 360 and/or the second compact bone wall of the first bone 360, and also adapted to maintaining the tensile force, so as to exert a force between the first compact bone wall of the first bone 360 and other bone portions.

The anchored hardware may be any of a variety of hardware, which may be anchored using a variety of different techniques and apparatus. The anchored hardware may generally be adapted to apply a compressive force to fracture 363 in the first bone 360, and/or to apply a compressive force between the first bone 360 and the dislocated second bone 365. In some embodiments, block 807 may be applied to treat a dislocation by anchoring hardware in the first compact bone wall of the dislocated second bone 365 as well as the second compact bone wall of the first bone 360, as mentioned above. In some embodiments, block 807 may be applied to treat fracture 363 by anchoring hardware in the second compact bone wall of the first bone 360, without necessarily anchoring hardware in dislocated second bone 365.

In some embodiments, block 807 may comprise removing tap apparatus 100 from bones 365 and 360, and inserting hardware in the holes tapped in bones 365 and/or 360. For example, tap apparatus 100 may be removed by turning the apparatus in an opposite direction as that used to advance apparatus 100. Hardware inserted into the holes tapped in bones 365 and/or 360 may comprise threaded hardware such as bolts with threads adapted to engage the spiral thread grooves in sidewalls of tapped holes in the compact bone walls. In some embodiments, the anchored hardware may comprise one or more sections of the articulated bone tap apparatus 100. For example, tap sections such as 131A and 131B may be allowed to remain in bones 365 and/or 360 as anchored hardware, while other portions of apparatus 100, such as sections 136A, 136B, and 137, may be removed from bones 365 and/or 360. Sections 136A, 136B, and 137 may optionally be coupled to allow removal of sections 136A, 136B, and 137 from bones 365 and/or 360, without removing one or more tap sections such as 131A. Block 807 may be followed by block 808.

At a "Couple Hardware" block 808, anchored hardware may be coupled to apply a compressive force across a dislocation or fracture 363. In embodiments adapted to treat a dislocation, anchored hardware in bones 365 and 360 may be coupled, e.g., by a member extending between the hardware anchored in the dislocated second bone 365 and the hardware anchored in the first bone 360. A compressive force may be applied between the anchored hardware, e.g., by shortening the coupling member, or by adjusting the anchored hardware, to compress bones 365 and 360 into a desired proximity, e.g., to draw bone 365 into contact with bone 360.

In embodiments adapted to treat fracture 363, anchored hardware in bone 360 may be coupled at block 808 with hardware located at the first compact bone wall of the first bone 360, e.g., by a member extending between the anchored hardware at the second compact bone wall of the first bone 360 and the hardware located at the first compact bone wall of the first bone 360. A compressive force may be applied between the anchored hardware and the hardware located at the first compact bone wall of the first bone 360, e.g., by shortening the coupling member, or by adjusting the hardware, to compress the segments of bone 360 to the right and left sides of fracture 363 into a desired proximity, e.g., to draw the left segment of bone 360 into contact with the right segment of bone 360.

The foregoing detailed description has set forth various embodiments of the devices and/or processes via the use of diagrams and examples. Insofar as such diagrams and examples contain one or more functions and/or operations, it will be understood by those within the art that each function and/or operation within such diagrams and examples may be implemented, individually and/or collectively, by a wide range of operational methods by appropriately trained professionals using a wide range of equipment.

Those skilled in the art will recognize that it is common within the art to describe devices and/or processes in the fashion set forth herein, and thereafter use engineering practices to integrate such described devices and/or processes into surgical and other medical therapies. That is, at least a portion of the devices and/or processes described herein may be integrated into a surgical therapy via a reasonable amount of experimentation. Those having skill in the art will recognize that surgical therapy generally includes one or more surgical steps and operational methods which are commonly known and understood to take place under the best medical and surgical practices. It is to be understood that the devices and operations disclosed herein are merely examples and that in fact many other devices and operations may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components.

Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically connectable and/or physically interacting components.

With respect to the use of substantially any plural and/or singular terms herein, those having skill in the art may translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While certain example techniques have been described and shown herein using various methods, devices and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter also may include all implementations falling within the scope of the appended claims, and equivalents thereof.

The invention claimed is:

1. An articulated bone tap apparatus, comprising:
   a bendable spine having a proximal end, a distal end, and a longitudinal axis, the spine comprising two or more sections extending from the proximal end along the longitudinal axis to the distal end;
   a movable bit engaged at the distal end of the spine;
   wherein longitudinal slide displacement of at least one of the two or more spine sections with respect to at least one other of the two or more spine sections is effective to steer the bit; and
   a flexible cylindrical tap sleeve adapted to at least partially encase the spine, wherein the tap sleeve and the bit are mechanically engaged so that rotation of the tap sleeve around the longitudinal axis of the spine is effective to rotate the bit.

2. The articulated bone tap apparatus of claim 1, wherein the tap sleeve is adapted to encase the spine between the bit and a proximal sleeve section at the proximal end of the spine, and wherein the tap sleeve comprises a plurality of rigid cylindrical tap sections arranged end to end along the spine, each tap section comprising an internal bore configured to house the spine, and each tap section comprising an external tap flute configured to cut a spiral groove into a sidewall of a hole cut by the bit as the tap sleeve rotates.

3. The articulated bone tap apparatus of claim 2, wherein adjoining tap sections are rotationally interlocked, wherein the tap sleeve and the bit are mechanically engaged by being rotationally interlocked, and wherein the tap sleeve and the proximal sleeve section are rotationally interlocked, so that rotation of the proximal sleeve section around the longitudinal axis of the spine also rotates the tap sleeve and the bit.

4. The articulated bone tap apparatus of claim 2, wherein adjoining tap sections are angularly adjustable to permit at least some degree of angular displacement between the adjoining tap sections.

5. The articulated bone tap apparatus of claim 2, wherein adjoining tap sections are rotationally interlocked by tapered cogs.

6. The articulated bone tap apparatus of claim 5, wherein the tapered cogs are of different lengths to produce gaps between the adjoining tap sections.

7. The articulated bone tap apparatus of claim 2, wherein the internal bores of the tap sections are of larger diameter than the spine, thereby providing an internal fluid conducting gap between the tap sleeve and the spine.

8. The articulated bone tap apparatus of claim 2, wherein the internal bores of the tap sections comprise one or more longitudinal grooves, thereby providing one or more internal fluid conducting grooves in the interior of the tap sleeve.

9. The articulated bone tap apparatus of claim 2, wherein the height of the tap flutes of the tap sections increases with distance from the bit.

10. The articulated bone tap apparatus of claim 2, wherein the tap sleeve comprises one or more rigid cylindrical spacer sections between the tap sections and the proximal sleeve section.

11. The articulated bone tap apparatus of claim 2, wherein the proximal sleeve section comprises a driver interface adapted to couple with a driver to apply torque to the tap sleeve.

12. The articulated bone tap apparatus of claim 1, further comprising a steering nut at the proximal end of the spine, wherein adjustment of the steering nut is effective to longitudinally displace the at least one of the two or more spine sections with respect to the at least one other of the two or more spine sections to steer the bit.

13. The articulated bone tap apparatus of claim 1, wherein the bit is rotatably attached to the spine so that the bit rotates independently from the spine.

14. The articulated bone tap apparatus of claim 2, wherein the bit comprises one or more cutting teeth, wherein at least one cutting edge of the bit is disposed on the one or more cutting teeth, wherein the one or more cutting teeth are adapted to cut the hole into surrounding material as the bit rotates clockwise, and wherein the one or more cutting teeth are adapted to cut the hole into surrounding material as the bit rotates counterclockwise.

15. The articulated bone tap apparatus of claim 1, wherein the bit comprises a sidewall hole.

16. The articulated bone tap apparatus of claim 1, wherein the spine is threaded.

17. A method for using an articulated bone tap apparatus to treat a bone fracture or dislocation, comprising:
   drilling a hole in a first compact bone wall of a first bone;
   inserting the articulated bone tap apparatus in the hole in the first compact bone wall, wherein the articulated bone tap apparatus comprises:
      a bendable spine having a proximal end, a distal end, and a longitudinal axis, the spine comprising two or more sections extending from the proximal end along the longitudinal axis to the distal end;
      a movable bit engaged at the distal end of the spine;
      wherein longitudinal slide displacement of at least one of the two or more spine sections with respect to at least one other of the two or more spine sections is effective to steer the bit; and
      a flexible cylindrical tap sleeve adapted to at least partially encase the spine, wherein the tap sleeve and the bit are mechanically engaged so that rotation of the tap sleeve around the longitudinal axis of the spine is effective to rotate the bit;
   turning the articulated bone tap apparatus to advance the articulated bone tap apparatus through a non-linear path within cancellous bone in the first bone to a second compact bone wall of the first bone;
   turning the articulated bone tap apparatus to advance the articulated bone tap apparatus through the second compact bone wall of the first bone and to tap a hole in the second compact bone wall of the first bone by cutting a spiral thread groove in a sidewall of the tapped hole in the second compact bone wall of the first bone; and
   anchoring hardware in the tapped hole in the second compact bone wall of the first bone, wherein the hardware is adapted to apply one or more of:
      a compressive force to a fracture in the first bone; or
      a compressive force between the first bone and a dislocated second bone.

18. The method of claim 17, wherein the anchored hardware comprises one or more sections of the articulated bone tap apparatus.

19. The method of claim 17, further comprising:
   inserting an articulated bone drill apparatus in the hole in the first compact bone wall;
   turning the articulated bone drill apparatus to advance the articulated bone drill apparatus through the non-linear path within cancellous bone in the first bone to the second compact bone wall of the first bone;
   turning the articulated bone drill apparatus to drill the tapped hole in the second compact bone wall of the first bone; and
   removing the articulated bone drill apparatus from the first bone.

20. The method of claim 19, further comprising turning the articulated bone drill apparatus to drill a hole in a first compact bone wall of the dislocated second bone.

21. The method of claim 17, further comprising:
   turning the articulated bone tap apparatus to advance the articulated bone tap apparatus through a first compact bone wall of the dislocated second bone and to tap a hole in the first compact bone wall of the dislocated second bone by cutting a spiral threaded groove in a sidewall of the tapped hole in the first compact bone wall of the dislocated second bone; and
   anchoring hardware in the tapped hole in the first compact bone wall of the dislocated second bone, wherein the hardware is adapted to apply the compressive force between the first bone and the dislocated second bone.

22. The method of claim 21, further comprising performing a closed reduction of the dislocated second bone prior to tapping the hole in the first compact bone wall of the dislocated second bone.

23. The method of claim 17, further comprising coupling the anchored hardware with hardware located at the first compact bone wall of the first bone and applying a compressive force between the anchored hardware and the hardware located at the first compact bone wall of the first bone to apply the compressive force to the fracture in the first bone.

24. The method of claim 17, further comprising flushing the articulated bone tap apparatus when turning the articulated bone tap apparatus to advance the articulated bone tap apparatus through the second compact bone wall of the first bone.

25. The method of claim 17, wherein the first bone comprises a bone in a human pelvis.

26. The method of claim 17, wherein the first bone comprises a human lower mandible.

27. The method of claim 17, further comprising establishing a location of the articulated bone tap apparatus using one or more of an ultrasound, X-Ray, or nuclear medicine imaging technique.

28. The method of claim 17, further comprising steering the articulated bone tap apparatus by adjusting the longitudinal slide displacement of the two or more spine sections within the articulated bone tap apparatus to direct the non-linear path of the articulated bone tap apparatus as the articulated bone tap apparatus advances within the cancellous bone in the first bone.

* * * * *

UNITED STATES PATENT AND TRADEMARK OFFICE
CERTIFICATE OF CORRECTION

PATENT NO. : 9,597,091 B2
APPLICATION NO. : 14/118626
DATED : March 21, 2017
INVENTOR(S) : Bromer It is certified that error appears in the above-identified patent and that said Letters Patent is hereby corrected as shown below:

In Column 1, Line 4, delete "CROSS-REFERENCE TO RELATED APPLICATIONS APPLICATION" and insert -- CROSS-REFERENCE TO RELATED APPLICATION --, therefor.

In Column 1, Line 7, delete "U.S.C. 371" and insert -- U.S.C. § 371 --, therefor.

Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*